United States Patent [19]

Gibby et al.

[11] Patent Number: 5,180,896

[45] Date of Patent: Jan. 19, 1993

[54] SYSTEM AND METHOD FOR IN-LINE HEATING OF MEDICAL FLUID

[75] Inventors: Gordon L. Gibby; Samsun Lampotang, both of Gainesville, Fla.; Daraius Hathiram, Houston, Tex.; Nikolaus Gravenstein, Gainesville, Fla.

[73] Assignee: University of Florida, Gainesville, Fla.

[21] Appl. No.: 595,472

[22] Filed: Oct. 11, 1990

[51] Int. Cl.$^5$ .............................................. H05B 6/64
[52] U.S. Cl. ....................... 219/10.55 A; 219/10.55 F; 219/10.55 R; 128/399; 128/804; 604/113; 606/33; 606/34; 606/42
[58] Field of Search ................ 219/10.55 A, 10.55 R, 219/10.55 B, 10.55 M; 128/400, 401, 402, 399, 804, 635, 636, 637; 604/113, 52, 114; 374/32, 116, 122, 132; 606/33, 34, 42

[56] References Cited

U.S. PATENT DOCUMENTS

| | | | |
|---|---|---|---|
| 2,407,690 | 9/1946 | Southworth | 128/804 |
| 3,092,514 | 6/1963 | Tomberlin | 219/10.55 A |
| 3,315,681 | 4/1967 | Poppendiek | 128/400 |
| 3,411,850 | 11/1968 | Williams et al. | 356/50 |
| 3,518,393 | 11/1968 | Besseling et al. | 219/10.41 |
| 3,698,813 | 10/1972 | Aisenberg | 356/48 |
| 3,920,945 | 11/1975 | Smith et al. | 219/10.55 R |
| 3,963,892 | 6/1976 | Camph et al. | 219/10.55 A |
| 4,152,567 | 5/1979 | Mayfield | 219/10.55 R |
| 4,222,663 | 9/1980 | Gebhart et al. | 356/45 |
| 4,400,097 | 8/1983 | Koschnitzke et al. | 374/121 |
| 4,532,414 | 7/1985 | Shah et al. | 128/399 |
| 4,566,804 | 1/1986 | Collins et al. | 219/10.57 |
| 4,664,515 | 5/1987 | Imura et al. | 356/43 |
| 4,747,826 | 5/1988 | Sassano | 604/52 |
| 4,759,749 | 7/1988 | Verkaart | 604/113 |
| 4,779,977 | 10/1988 | Rowland et al. | 356/45 |
| 4,818,102 | 4/1989 | Glenn | 356/43 |
| 4,874,033 | 10/1989 | Chatelain et al. | 128/400 |
| 4,940,865 | 7/1990 | Johnson et al. | 219/10.55 A |
| 4,974,592 | 12/1990 | Brauco | 128/635 |
| 4,989,606 | 2/1991 | Gehrich et al. | 128/637 |
| 5,047,208 | 9/1991 | Schweitzer et al. | 128/634 |
| 5,073,167 | 12/1991 | Carr et al. | 128/804 |

OTHER PUBLICATIONS

"Preventing Hypothermia in Trauma Patients by Microwave Warming of IV Fluids", J. Antonio Aldrete, pp. 435–442, Nov. 14, 1985.

"Rapid Controlled Thawing of Fresh-Frozen Plasma in a Modified Microwave Oven", Rock et al, pp. 60–65, Mar. 31, 1983.

"Testing of a New In-Line Blood Warmer", Linko, pp. 445–446, 1980.

"Erythrocyte Damage Caused by the Haemotherm Microwave Blood Warmer", Linko and Hynynen, pp. 320–328, 1979.

"Influence of the Taurus Radiowave Blood Warmer on Human Red Cells", K. Linko and R. Hekali, pp. 46–52, 1980.

"Radiowave and Microwave Blood Warmers: Comparison with Water Bath Blood Warming Units", Hamid Dalili et al, Southern Medical Journal, Nov. 1973, vol. 66, No. 11, pp. 1254–1259.

Primary Examiner—Bruce A. Reynolds
Assistant Examiner—Tuan Vinh To
Attorney, Agent, or Firm—Kerkam, Stowell, Kondracki & Clarke

[57] ABSTRACT

The heating of blood or other medical fluids supplied to a patient is provided by a system and method of feedback control. The temperature of the blood is sensed by receiving infrared energy from the medical fluid as it flows within a sterile and disposable tube from a fluid source to the patient. Feedback control stabilizes the temperature at a desired value. A second sensor may optionally be used to determine if the fluid is too hot within the microwave device itself. The disposable tube has at least one window or thin membrane portion which allows infrared radiation to pass therethrough in order to be sensed by the sensor. One arrangement of the present invention uses a microprocessor with adaptive control to provide precise and accurate control of the temperature of the medical fluid.

3 Claims, 5 Drawing Sheets

SYSTEM AND METHOD FOR IN-LINE HEATING OF MEDICAL FLUID

BACKGROUND OF THE INVENTION

This invention relates to a system and method for in-line heating of medical fluid supplied to a patient.

In numerous medical procedures it is necessary to supply medical fluid to a patient. The medical fluids often are blood or blood products. Saline, anesthetics and other medical fluids are also commonly supplied to patients undergoing medical procedures.

Warming fluids is a major problem in the operating room particularly in abdominal surgery, prolonged surgery and all major trauma surgery. Because the surgeon is in a gown he prefers the room quite cool (typically 60 degrees F.) to prevent sweat from falling into the wound. The patient, under anesthesia, loses most abilities to regulate his own temperature. Then cold intravenous fluids are infused and the patient becomes colder and colder as the operation proceeds. If major blood loss or "third spacing" of fluids occur, the patient will typically lose several degrees of temperature within two hours. If the patient becomes colder than 34 degrees centigrade, many anesthesiologists will not extubate the patient and prefer to leave the patient intubated and mechanically ventilated because of the deleterious effects of cold on mental status and respiratory muscle strength in the face of resolving neuromuscular blockade. Effects of cold on clotting become more noted at lower temperatures, as does the tendency toward ventricular arrhythmias. Below 32 degrees, the patient stands a great chance of a fatal ventricular arrythmia and certainly problems from inadequate cardiovascular performance. Patients die from this type of cold.

Warming fluids from their storage temperatures (usually 4° C. for blood and blood products) to normothermic or even slightly hyperthermic temperatures is a well-recognized way to deal with this problem. Current recommended practice is to use blood warmers to bring blood to about 37° C., which is body temperature. Unfortunately, for the patients who need it most, the usual fluid warming device fails, because it cannot handle adequately fluid flows greater than 100 cc/min. Typically the conduction heating devices result in fluids of lower and lower temperatures as the flow rate increases.

Common complaints about existing blood warmers is that they have high flow resistance, do not warm the blood enough, are difficult to prepare, are too expensive, too bulky, and present risks of infection of the blood and risks of spillage of blood products in the operating room because of large surface area, thin-walled reservoirs for heat transfer. The poor performance of available equipment contributes to undesired hypothermia of patients, a known cause of delays in awakening after surgery which needlessly increases the (expensive) time the patient must spend being intensively monitored in a recovery room and delays the ability for a full mental and neurologic assessment of the patient to be made after surgery. Cold patients are a real problem from all perspectives.

The existing blood/fluid warmers fall into broad categories of in-line warmers which heat fluid flowing in a path to the patient and batch warmers which heat fluid in a batch, the fluid then being placed in a separate delivery system for supplying the patient. Warmers fall into the following more specific categories:
  (a) Water Bath
  (b) Dry Heat
  (c) Microwave
  (d) Radiowave The first two of the four specific categories are usually inline blood warmers and depend on conduction as the main mode of heat transfer. The latter two categories are usually batch type warmers, i.e., they are not in-line warmers (but an in-line microwave warmer is discussed below). The microwave warmer uses electromagnetic radiation of 2450 MHz to excite the vibration mode of the water molecules to produce heat. The radiowave warmer uses a different frequency (27 MHz), and therefore a longer wavelength of electromagnetic radiation to warm the blood. It is also worth noting that, as far as known, none of the existing commercial blood warmers exploit the powerful flexibility and versatility of microprocessors to control the infusion temperature. The four categories will be discussed in turn.

(a) Water Bath Blood/Fluid Warmers

Blood flows in a coil, made of polythene tubing, that is immersed in a stirred warm water bath at 35-37 degrees C. The water bath is heated by an electric heater element and sensors monitor the temperature of the water bath. In older simpler models, warm water from the tap is used for the water bath and there is no in-built heater. It is surprising to note that the temperature of the blood/fluid at the outlet of the warmer is not monitored. Current blood/fluid warmers of this type are the Level 1 (Patent pending), Dupaco Hemokinethitherm and Jensen 709-100-1. The Level 1 warmer (a countercurrent heat exchanger using water at 40° C. as the heating medium) is currently considered as the best in-line blood warmer.

The Level 1 Fluid Warmer is a known commercial product which was developed to meet this need, using an improved conduction heating system. Quite formidable in size, weight and cost, this device also involves the use of a very expensive disposable, limiting its usage for all but the most desperate cases. The disposable is a portion of the system which is in contact with the blood or other fluid and which must be replaced to use the system on a new patient. It claims the ability to warm "cold blood" at 500 cc/min and room temperature solutions at 1000 cc/min. A smaller, somewhat less expensive device and disposable are able to handle half this capacity, or 250 cc/min cold blood. Unfortunately, the disposable still has a very significant price because of its complex heat transfer device.

The warm water bath is a perfect medium at the right temperature for growing bacteria. In a study, cultured samples from water baths yielded Bacillus species in 72% of the samples, Flavobacterium species in 39% and Pseudomonas species in 9%. These bacteria can contaminate the administered fluid or blood by gaining entry at the connections between the tubing and the coil. A fatal case of Pseudomonas septicaemia in a patient given fresh frozen plasma warmed in a water bath contaminated with *Pseudomonas aeruginosa* is reported in the literature.

The design of a water bath blood warmer uses a circuitous pathway for heating blood: the electric heater element heats the water, the water heats the polythene coil, the polythene heats blood close to the tubing wall and the heat from the blood layers close to the polythene walls is then transferred to the blood in the center of the tube. The multiple layers of thermal resistance interposed between the heat source and the fluid to be warmed decrease the efficiency of the system. Further, polythene is a relatively poor conductor so that there is a significant temperature gradient across the polythene wall.

In the water bath warmer, to ensure that the fluid in the center of the tube is rapidly warmed by the fluid in contact with the tubing wall, the distance between these two layers of fluid is minimized by using small bore tubing (3/16" internal diameter). Since the residence time of the fluid in the water bath must be sufficient for the fluid to absorb enough heat, a long length of tubing is used to generate the required dead space and hence the desired residence time. This long length of small bore tubing causes appreciable flow resistance which limits the flow rate that can be passed through the warmer when using gravity feed. Using a 58 per cent glycerol water solution to simulate blood, the Portex coil (a commonly used coil in water bath warmers) showed a pressure drop of 19 torrs at a flow rate of 22.4 mL/min and 48.3 torrs at 56.5 mL/min. Flow rates of up to 250 mL/min are sometimes required and the pressure drop across the tubing would then be excessively high since flow resistance as well as pressure drop increases with flow rate in real systems.

With the water bath heater, at steady state, the mean infusion temperature of the fluid decreases as the flow rate increases. With cold water at 5° C. at the inlet, the mean outlet temperature dropped from 36° C. at a flow rate of 150 mL/min to 28° C. at 340 mL/min. This steep degradation in performance at increased flow rates can be explained by the shorter residence time of the blood in the water bath at higher flow rates. Less heat can be transferred to a given volume of fluid because there is less time during which heat transfer can take place. It is interesting to note that the plot for mean outlet temperature versus flow rate is linear within experimental accuracy. This is not surprising since mean outlet temperature is proportional to heat transfer which is proportional to residence time which is inversely proportional to flow rate. However, it is alarming that at high infusion flow rates, the degradation in performance of water bath blood warmers means that large volumes of fluid significantly below the recommended minimum infusion temperature (32° C.) are being administered, thus increasing the risk of fibrillation.

The cooling of the fluid as it flows from the warmer to the catheter is not taken into account in the water bath systems.

In a water bath blood warmer, the thermal inertia of a large mass of water is required to damp out temperature fluctuations. Therefore, the system is necessarily bulky, heavy and unwieldy to use. The water bath can spill and overflow, creating slippery and electrically unsafe conditions in the operating room.

The long pathway that the heat takes before getting to the blood creates a pure time delay between the control action (cause) and the response (effect). Pure time delays are undesirable in closed loop control systems since they destabilize the system especially if the time delay is large enough that the error signal is 180° out of phase with the reference input.

(b) Dry Heat Blood/Fluid Warmers

As the name implies, the dry heat blood warmers do not use a water bath. Instead, metal (usually aluminum) surfaces in intimate contact with a plastic cuff (e.g. American Pharmaseal DW-1000) or tube (DataChem Inc. FloTem II, U.S. Pat. No. 4,532,414) are heated by electric heater elements and transfer heat to the fluid by conduction via the plastic. Thermostats monitor the temperature of the metal surfaces in contact with the plastic containing the blood and turn the heaters on and off accordingly. Here again, the outlet temperature of the fluid is not monitored. In general, the performance of dry heat warmers is inferior to the water bath warmers. Other current dry heat blood warmers are the Electromedics BT-794, Fenwal BW-5 and the Mallinckrodt Animec.

Flow resistance is typically high in dry warmers. Since conduction is the main mode of heat transfer in dry heat blood warmers, the cuff or tubing has to be of narrow bore which increases flow resistance and limits the amount of flow available with gravity feed. The cuff used with the Gorman-Rupp DW 1220 blood warmer exhibited 1.8 times the flow resistance of the Portex coil used in water bath blood warmers: 34 torrs pressure drop at an infusion flow rate of 22.4 mL/min and 85.7 torrs at 56.5 mL/min. With the American Medical Systems DW-1000 cuff, the maximum flow rate with gravity feed is 200 mL/min according to the manufacturer. We could get a maximum flow rate of only 150 mL/min with gravity feed from a standard saline bag mounted four feet above the cuff and connected to the blood warmer via a Y-type blood-solution recipient set with large filter (Fenwal code 4C2132).

Heat transfer to the blood is ineffective in a dry warmer. The cuff in the Gorman-Rupp DW 1220 and the tube in the DataChem FloTem II are heated from one side only. In tests conducted with 5° C. water, the heating efficiency of the DW 1220 was found to be inferior to the Portex coil in a warm water bath maintained at 36.8° C. with a thermostat. The mean outlet temperature dropped to 32° C. at a flow rate of 157 mL/min for the DW 1220 and 228 mL/min for the Portex coil. For the FloTem II, the manufacturer's specifications state that when supplied with 4°-6° C. water, the outlet temperature will be 33° C. at a flow rate of 5 mL/min, 29° C. (below the recommended minimum of 32° C.) at 25 mL/min and room temperature of 100 mL/min.

In dry heat warmers, the steady state outlet temperature of the fluid is a function of the flow rate. When supplied with 5° C. water at the inlet, the mean outlet temperature drops from 33° C. at a flow rate of 100 mL/min to 27° C. at 290 mL/min.

Plastic is a poor conductor and causes a large temperature drop between the heated metal surface and the fluid in the cuff or tube in dry warmers. Since the temperature of the heated surface, instead of the outlet temperature of the fluid is being monitored, there is a temperature offset which results in the temperature of the fluid at the outlet being colder than the heated surface.

The cooling of the fluid as it flows from the warmer to the catheter is not taken into account in dry warmers.

The thermal inertia of the heated metal surface and the plastic create pure time delays which degrade the response time of the system to a change in operating conditions. The pure time delays make it difficult to use a closed loop control system with dry heat warmers.

In the dry heat blood warmer, the cuff is made of thin plastic to improve heat transfer. However, this also makes it very easy to rupture the cuff and spill its contents.

(c) Microwave Blood Warmer

The literature on blood warmers mentions two microwave blood warmers (Haemotherm Universal and Haemotherm B), both manufactured by Robert Bosch Elektronik GmbH, Berlin, West Germany. The Haemotherm Universal and Haemotherm B are of similar construction; the only technical difference is that the Universal can warm both blood bottles and bags whereas the B warms blood bags only. The warmers operate at a frequency of 2450 MHz, with a rated power output of 400 W developed by two magnetrons. The blood unit is placed in an insulated chamber where it is continuously mixed by a 350° rotation around its cross-axis to prevent hot spots due to non-uniform distribution of the microwave radiation. A temperature probe on the surface of the bag monitors the blood temperature by inference and switches off the magnetrons when the temperature reaches a preset value. Warming is also interrupted if the stirring mechanism fails or if the chamber is opened.

A study showed that "microwaves per se are not harmful to erythrocytes but that poor penetrance of microwaves, together with insufficient blood mixing during warming, are the critical factors leading to hemolysis."

U.S Pat. No. 3,963,892 of Camph et al issued Jun. 15, 1976 shows in-line heating by microwaves of blood being passed from a container to a patient.

The Haemotherm is a batch heater. The blood unit will cool down to room temperature if it is not immediately administered to the patient or if it is administered at low flow rates.

Blood units are about three inches thick at the widest point and the depth to which microwaves can penetrate in blood is ½ to 1 inch when batch microwave heating is performed. To prevent hot spots and ensure that blood in the center of the unit is exposed to microwave radiation, the blood unit needs to be continuously mixed by a rotating action. Even with rotation of the bag, there are hot spots and consequently hemolysis at the corners of the bag because there is flow stagnation at the corners.

The in-line microwave heating of the Camph patent avoids some of the batch heating problems. However, it would be relatively expensive to produce as it apparently would use thermocouple measurement of blood temperature flowing past the microwave. The thermocouple would have to be manufactured as part of the sterile fluid path of the blood to have reasonable degree of accuracy and would have to be calibrated and connected to the system, all in sterile fashion. Further, the thermocouple wires can provide a nidus for clotting or allow electrical leakage currents to enter the blood. Possibly, the wires might allow pieces of wire to be carried away in the blood.

(d) Radiowave Blood Warmers

The Taurus model 300 radiowave blood warmer is manufactured in England by the Plessey Group. Blood is warmed by radiowave energy. A mixing mechanism consisting of a blood unit between two circular condenser plates which oscillate back and forth through an angle of 120 degrees at a rate of 50 rpm ensures uniform heat distribution. Blood temperature is monitored from the surface of the bag by a probe mounted in the center of one of the condenser plates. Warming is discontinued when the temperature reaches a preset value or if the temperature sensor or the mixing mechanism or the cooling fan is damaged. The device will not operate if there is no blood in the chamber or if the door is open.

The radiowave blood warmer is a batch-type warmer and consequently suffers from the disadvantages of batch warming. Some researchers have reported alterations resembling those of aging of blood which were more obvious after warming with radiowaves than with microwaves.

OBJECTS AND SUMMARY OF THE INVENTION

Accordingly, it is a primary object of the present invention to provide an improved method and system for warming medical fluids, such as blood, which are supplied to a patient.

A further object of the present invention is to provide fluid warming by use of a relatively low cost disposable element.

Yet another object of the present invention is to provide medical fluid warming with a relatively low risk of infection.

A still further object of the present invention is to provide blood warming by use of relatively low cost apparatus.

Further objects of the present invention include avoiding and/or minimizing the disadvantages discussed above with respect to various prior techniques.

The above and other objects of the present invention which will become more apparent as the description proceeds are realized by a system for in-line heating of medical fluids supplied to a patient including a heating apparatus for radiant heating by electromagnetic radiation having a source of the electromagnetic radiation, a housing, and a zone for heating within the housing. The housing has an inlet for entry of medical fluids into the zone while the source is generating electromagnetic radiation and an outlet for exit of medical fluid while the source is generating electromagnetic radiation for heating medical fluid flowing in a path between the inlet and outlet. A first sensor senses the temperature at a first location of medical fluid heated by the heating apparatus and generates a first output representative of sensed temperature. The first sensor senses temperature by receiving waves of energy. A controller receives the first output and provides feedback control of the source to minimize differences between the sensed temperature of the medical fluid and a desired temperature before the medical fluid. A tube carries medical fluid therein at least in the zone between the inlet and the outlet and defines a path. The first sensor senses temperature by non-conductively receiving waves of energy (i.e., at least some mechanism beyond simple electric conduction and beyond simple thermal conduction is used to provide a substantial portion of the energy supplied to the first sensor (from at least one of the tube and the medical fluid at the first location.) The first sensor is separate from the tube in that it is not within the tube or within a wall of the tube. The tube includes accommodation means at the first location, the accommodation means providing (i.e., either directly or allowing the transmission therethrough) the waves of energy to the first sensor. The first sensor preferably senses temperature by receiving optical waves of energy, at least some of which have passed through at least part of the accommodation means. The first sensor senses temperature by receiving infrared waves of energy, at least some of which are from the medical fluid and have radiantly propagated to outside of the tube. The system may further comprise a second sensor which senses temperature by receiving infrared waves of energy at least some of which are from the medical fluid and have radiantly propagated to outside of the tube. The second sensor has a second output which is dependent on the temperature of the medical fluid at a second location and the second output is received by the controller. At least one of the first and second locations is preferably within the zone and a corresponding one of the first and second sensors receives infrared waves of energy which radiantly travel from within the zone to outside of the zone. The heating apparatus is preferably a microwave apparatus, the source is a microwave source, and the zone is a microwave cavity. The system may further comprise a first waveguide at the inlet and a second waveguide at the outlet, each of the first and second waveguides allowing medical fluid flow through the microwave cavity, while minimizing microwave leakage. A third waveguide may allow infrared energy emitted from medical fluid within the microwave cavity to pass out of the microwave cavity to one of the first and second sensors. The tube includes a thin membrane portion to allow infrared energy to pass therethrough to the first sensor. The first sensor non-invasively senses the temperature of medical fluid in the tube, meaning that the sensor itself or any portion thereof does not extend inwardly from the normal inner wall of the tube. The controller is preferably a microprocessor and provides adaptive control of the system. The tube is a disposable sterile tube removably positioned at least partly within the zone.

The method of the present invention may be described as a method of in-line heating of medical fluids being supplied to a patient and including the step of causing medical fluid flow through a heating apparatus to a patient, the heating apparatus having a source of electromagnetic radiation, a housing, and a zone for heating within the housing, the medical fluid flowing in a tube extending in between an inlet and an outlet of the housing. The medical fluid is then heated as it flows through the zone by operation of the source. A first sensor is used to sense, at a first location, the temperature of the medical fluid which has been heated in the zone, the first sensor sensing temperature by non-conductively receiving waves of energy and generating a first output representative of sensed temperature. The first output is then supplied to a controller. The controller provides feedback control of the source to minimize differences between the sensed temperature and a desired temperature of the medical fluid. The heating apparatus is a microwave apparatus and the first sensor senses infrared energy from medical fluid within the tube.

The invention may further be described as a tube for carrying medical fluid, the tube having a thin membrane portion thinner than a remainder portion of the tube and allowing passage of infrared energy from medical fluid therein to outside of the tube. The tube is disposable and adapted for being removably positioned in a microwave apparatus.

BRIEF DESCRIPTION OF THE DRAWINGS

The above and other features of the present invention will be more readily understood by reference to the drawings in which like characters represent like parts throughout the several views and in which.

DETAILED DESCRIPTION

Figure 1:
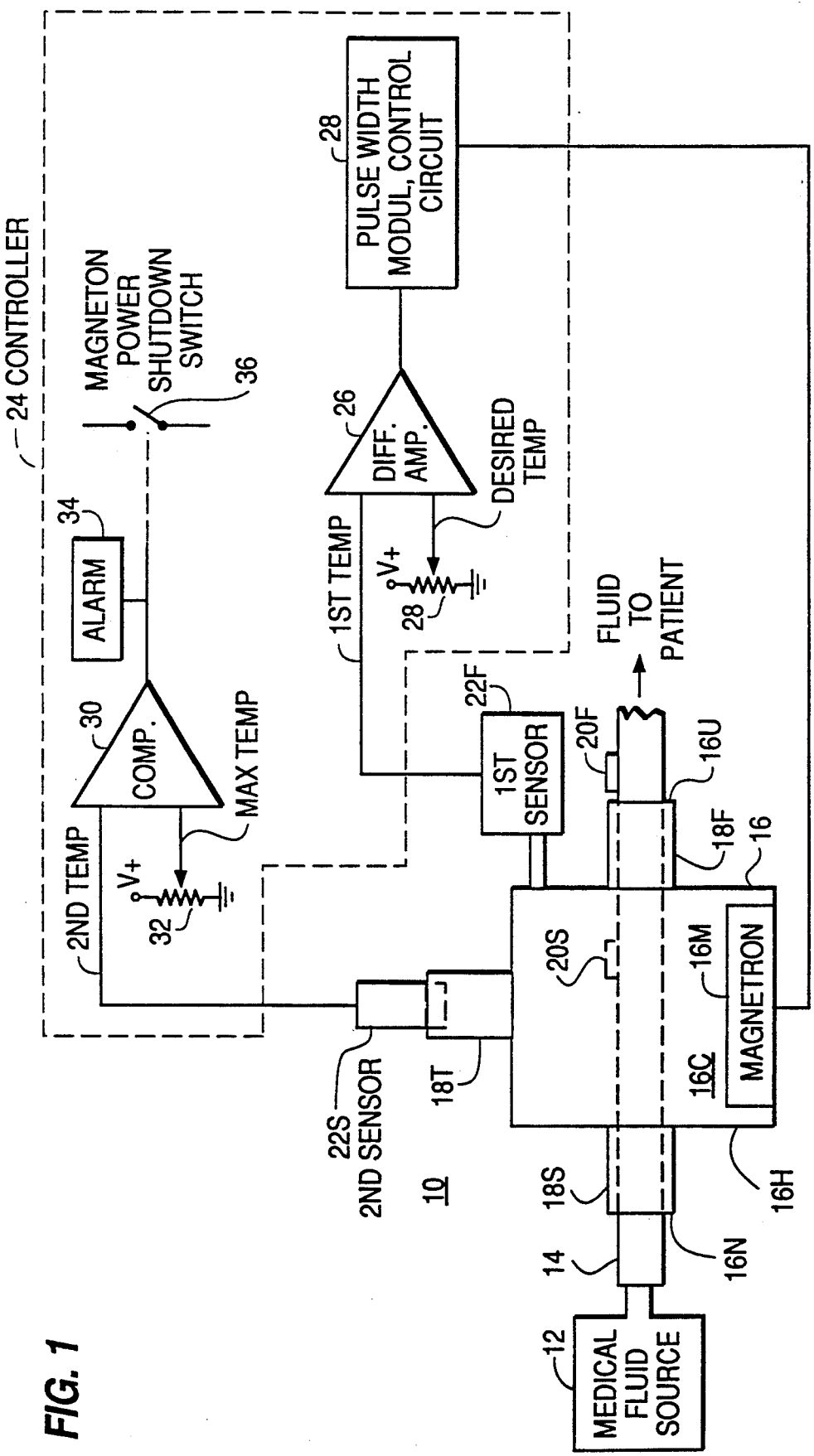
FIG. 1 shows a schematic and simplified view of a circuit embodiment of the present invention.

With reference now to FIG. 1, the system 10 is adapted to provide medical fluid from a source 12 to a patient (not shown). The medical fluid, which may be blood, blood products, saline, or other medical fluid supplied for the treatment of patients (usually human, but could be animals as well). The medical fluid flows in a tube 14 which extends from the fluid source 12 to a catheter (not shown) for supplying the fluid as an IV fluid or otherwise to the patient. The simplified view of FIG. 1 does not show various known components used for supplying fluid from a source to a patient. As the present invention relates to the heating of fluid which is supplied to the patient, the present discussion will concentrate on the heating arrangement.

As shown in FIG. 1, the tube 14 extends through a microwave apparatus 16 having a magnetron 16M, a housing 16H, and defining a microwave cavity 16C. The tube 14 enters the microwave apparatus 16 by way of an inlet 16N and exits the microwave apparatus by way of an outlet 16U.

Mounted at the outlet 16U and the inlet 16N are corresponding first and second waveguides 18F and 18S respectively. Each of the waveguides is a cylindrical tube made of copper or other conductive material. These waveguides 18F and 18S are used to allow fluid flow to and from the microwave, while blocking leakage of microwaves. They operate based upon the principle that a cylindrical waveguide cannot support microwave fields if its size is smaller than a certain fraction of the wavelength. In similar fashion, the hundreds of holes in the front of a common microwave oven door do not leak microwaves. In the preferred embodiment of the present invention, the waveguides 18F and 18S will have a cutoff frequency of 9 GHz such that there is very little leakage at the microwave frequency of 2.54 GHz.

In addition to having a diameter selected to prevent microwave leakage based upon the above considerations and using known relationships for waveguides, the length of the waveguide is preferably one-fourth of the wavelength of the microwaves. By using a waveguide of such a length, the waveguides reflect back the open circuit of the open end hole back to the cavity as a short circuit. In other words, the microwave cavity "sees" the cavity housing as a solid wall without any holes therein.

The tube 14 may be a commonly used sterile plastic tube, such as TYGON, except that the tube has significant modifications as will be discussed. In particular, thin membrane or window portions 20F and 20S are mounted to the tube 14. Each of the windows 20F and 20S is sufficiently thin as to allow a significant portion of infrared energy to escape from the medical fluid flowing within the tube 14, the infrared energy from the first location corresponding to window or thin membrane portion 20F being supplied to a first sensor 22F and the infrared energy from a second location corresponding to the second window or thin membrane portion 20S being supplied to a second sensor 22S.

Figure 2:
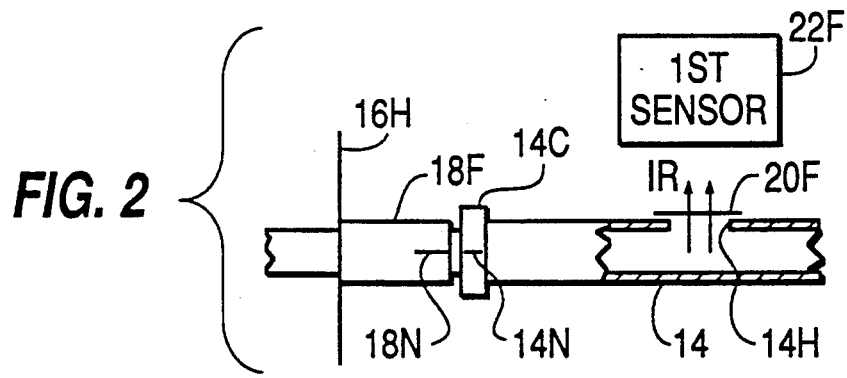
FIG. 2 shows an enlarged view with portions broken away of a portion of the system of FIG. 1.

Before discussing the operation of the sensors, reference is made to FIG. 2 showing the tube 14, the first waveguide 18F, and the side of the microwave housing 16H. As shown in FIG. 2, the window or thin membrane portion 20F is a membrane which is stretched tightly and bonded as by gluing to the remainder thicker portion of the tube 14. The thin membrane 20F may be a circular membrane covering a corresponding circular hole 18H. The thin membrane portion of the tube 14, preferably has a thickness of 2 mils or less and, most preferably, is approximately 1.5 mils in thickness. The thin membrane 20F allows a large portion of the infrared radiation of the fluid within tube 14 to be radiated outwardly as shown for sensing as by sensor 22F. Further, the thin membrane will, by conduction, track the temperature of the fluid touching it fairly accurately because of the relatively large area of the membrane in direct contact with the fluid and the thinness of the membrane. The membrane will equilibrate with the fluid temperature and give off its own infrared radiation which will also be sensed by the sensor 22F to obtain a temperature reading. It should be noted that the material for the thin membrane portion 20F may be the same material as the tube 14 or some other commonly used medical plastic. Although the thin membrane portion has been shown as a membrane which is bonded to the remainder of the tube 14, the thin membrane portion 20F could alternately be made integrally with the tube 14. The window 20S of FIG. 1 would, of course, be constructed identically to the window or thin membrane portion 20F described in detail with respect to FIG. 2.

In addition to having the thin membrane portion 20F, the tube 14 may, optionally, have some arrangement to allow the tube 14 to bring the window 20F in registry with the sensor 22F. In the arrangement of FIG. 2, a collar member 14C is disposed on the tube 14 and includes an indicia 14N which lines up to an indicia 18N which is disposed upon the waveguide 18F. When the ring or collar 14C is disposed directly against the outside of waveguide 18F and the indicia 14N and 18N are lined up, the window 20F will be properly disposed relative to the first sensor 22F. Likewise, the window 20S would then be properly disposed (refer to FIG. 1) relative to the second sensor 22S. Various other arrangements could be used for placement of the window or thin membrane portion 20F in registry with the first sensor 22F, such arrangements including latching and locking means if desired.

Referring back to FIG. 1, the first and second sensors 22F and 22S may be a known commercial sensor for receiving infrared energy from an object and providing an electrical output signal representative of the temperature of the object. The sensors sense the "black body" infrared energy or radiations given off by all objects. In the preferred embodiment, the first and second sensors use a probe with microdeposited thermocouples and an infrared lens which allows quick and accurate temperature measurement without any physical contact required. This is quite significant since the sensors may be separate from the tube 14 and the tube 14 may be made of relatively inexpensive materials. The tube 14 must be sterile and should be disposed of after each use. In other words, the avoidance of a necessity for physical contact between the sensor and the medical fluid and tube is quite an improvement over arrangements which require a thermistor or other relatively expensive element buried in the tube. The first and second sensors may be infrared digital temperature monitors model DTM290C with modified analog output, 10 millivolts per degree centigrade, made by Exergen Corporation of Natick, Mass.

The output of the first sensor 22F is a first output corresponding to the first temperature. That first output is supplied to a controller 24 including numerous subcomponents which will be discussed presently. The first output (labeled "1st TEMP" in FIG. 1) is supplied to a differential amplifier 26 which compares the measured temperature to a desired temperature established by a potentiometer 28 which a human operator has set to correspond to the desired temperature. The output from the differential amplifier is an error signal fed to a pulse width modulation control circuit 28. The pulse width modulation control circuit 28 may use known principles of duty cycle control to vary the pulses, thereby adjusting the power of the magnetron 16M which is controlled thereby. Essentially, if the output of differential amplifier 26 indicates that the measured temperature is below the desired temperature, the pulse width will be increased. However, if the first temperature is above the desired temperature, the pulse width control circuit 28 will decrease the width of the pulses supplied to the magnetron 16M. In that fashion, the arrangement provides feedback control of the magnetron 16M and tends to maintain the temperature of the medical fluid at the first window or thin membrane portion 20F at a temperature identical or very close to the desired temperature which had been established by the human operator by adjustment of the potentiometer 28.

The second sensor 22S may be mounted in a third waveguide 18T on the housing of microwave oven or apparatus 16. The third waveguide 18T may be constructed in identical fashion to the first and second waveguides 18F and 18S. The second sensor 22S may be mounted above the waveguide 18T or may be mounted partially within the waveguide as shown. The sensor 22S supplies a second output corresponding to a second temperature at a second location having the window or thin membrane portion 20S. The output from sensor 22S is fed as one input to a comparator 30. The other input of the comparator 30 is a signal representing the maximum temperature as set by a human operator by adjusting a potentiometer 32. If the sensed temperature is greater than the maximum temperature, the comparator 30 will trigger an alarm 34 and will shut off a magnetron power shut down switch 36. Additionally, the presence of an excessive temperature could be used to turn down other components in the system, which components are not shown. For example, any pump used in pumping the medical fluid could also be shut down under those circumstances.

By using the two sensors 22F and 22S, one of the sensors may provide feedback control of the magnetron, whereas the other sensor is used to directly sense the temperature of the fluid inside of the microwave cavity 16C. Further, the use of two sensors allows one to better detect an error mode such as when the flow has ceased. Under those circumstances, the sensor 22S will detect a significant increase in temperature.

Figure 3:
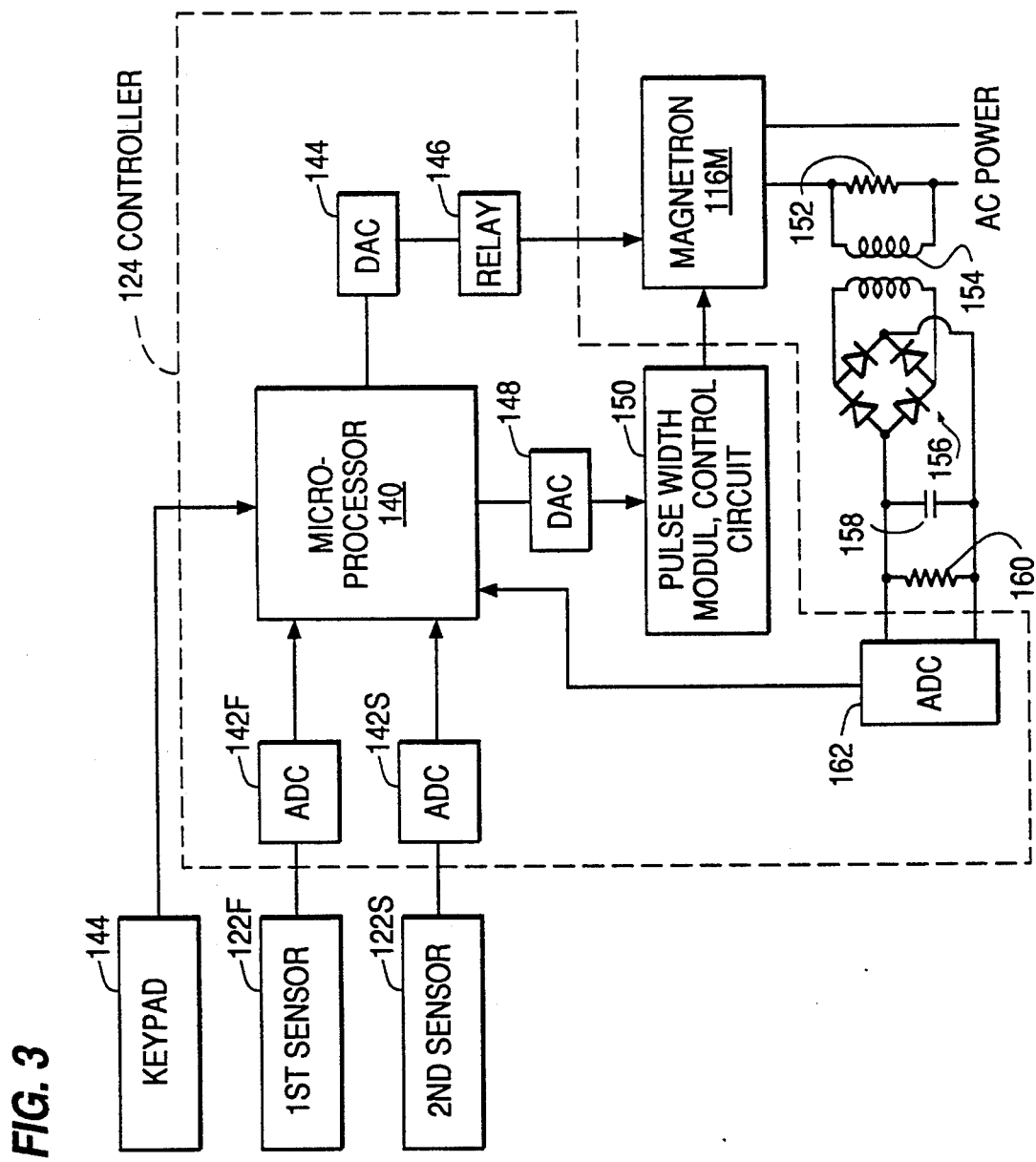
FIG. 3 shows a blocked diagram of a microprocessor embodiment of the present invention.

Turning now to FIG. 3, there is shown an alternate embodiment of the present invention. In particular, the arrangement of FIG. 3 uses a controller 124 having a microprocessor 140 disposed therein.

The components of FIG. 3 are labeled with numbers in the "100" series having the same last two digits as the corresponding component, if any, of the arrangement of FIG. 1. The first sensor 122F and second sensor 122S would operate in the same fashion as discussed with respect to FIGS. 1 and 2. The tube 14 is not shown in FIG. 3, but would be identical for this embodiment of the invention. The outputs from the sensors 122F and 122S are fed to the microprocessor 140 by way of analog to digital converters 142F and 142S. Additionally, a key pad 144 is connected to the microprocessor 140 and is used to input the desired temperature and otherwise control the microwave apparatus (only the magnetron 116M is shown in FIG. 3). The microprocessor 140 may turn on the magnetron 116M by way of a digital to analog converter 144 and a relay 146. Additionally, the microprocessor 140 may control the power of the magnetron 116M by way of a digital to analog converter 148 connected to a pulse width modulation control circuit 150. The details of the pulse width control circuit and the control of the magnetron 116M may be accomplished using known arrangements except that changes from known arrangements will be discussed hereafter.

In order to avoid an observed two degree jump in "measured temperature" whenever the microwave goes on caused by the interference of the microwave, the arrangement of FIG. 3 measures the actual temperature during intervening times when the microwave is off. Additionally, there is a problem in accurately controlling the heat of the magnetron due to the fact that the magnetron takes a variable amount of time to power up and produce microwave power. If the magnetron had been on in the last few seconds, then its turn on delay will be less. However, if the magnetron has not been on for some time, the turn on delay can be quite large, up to three seconds.

The delay in turn on of the microwave is composed of two parts. The majority is the delay due to the warming up of the filament. The present invention may readily avoid that delay by running the filament continuously. However, the second part of the delay is the unpredictable time that it takes for the oscillations to build up in the magnetron. Thence, the present invention will, unlike a microwave oven as used for cooking, require precise control of temperature. The fluid flowing through the microwave cavity makes it quite important to be able to adjust the magnetron power based not only on the temperature at which the fluid is to be disposed, but also taking into account the variations in the time from the supplying of a pulse to the magnetron and the actual start of microwave power generation.

By observing the operation of the microwave, the present inventors have developed a technique for providing precise power. Specifically, the present invention may measure the current in the A/C line going to the microwave oven. When the fans and similar portions of the circuit are operating, it draws only a small amount of power. When the magnetron is energized, there is an additional small amount of power due to the filament. However, after a delay, there is a large increase in the power as the magnetron begins to oscillate and draw current. By detecting when the large increase in power occurs, one can determine the time lag from the application of power to the magnetron and the start of microwave power generation.

Figure 4:
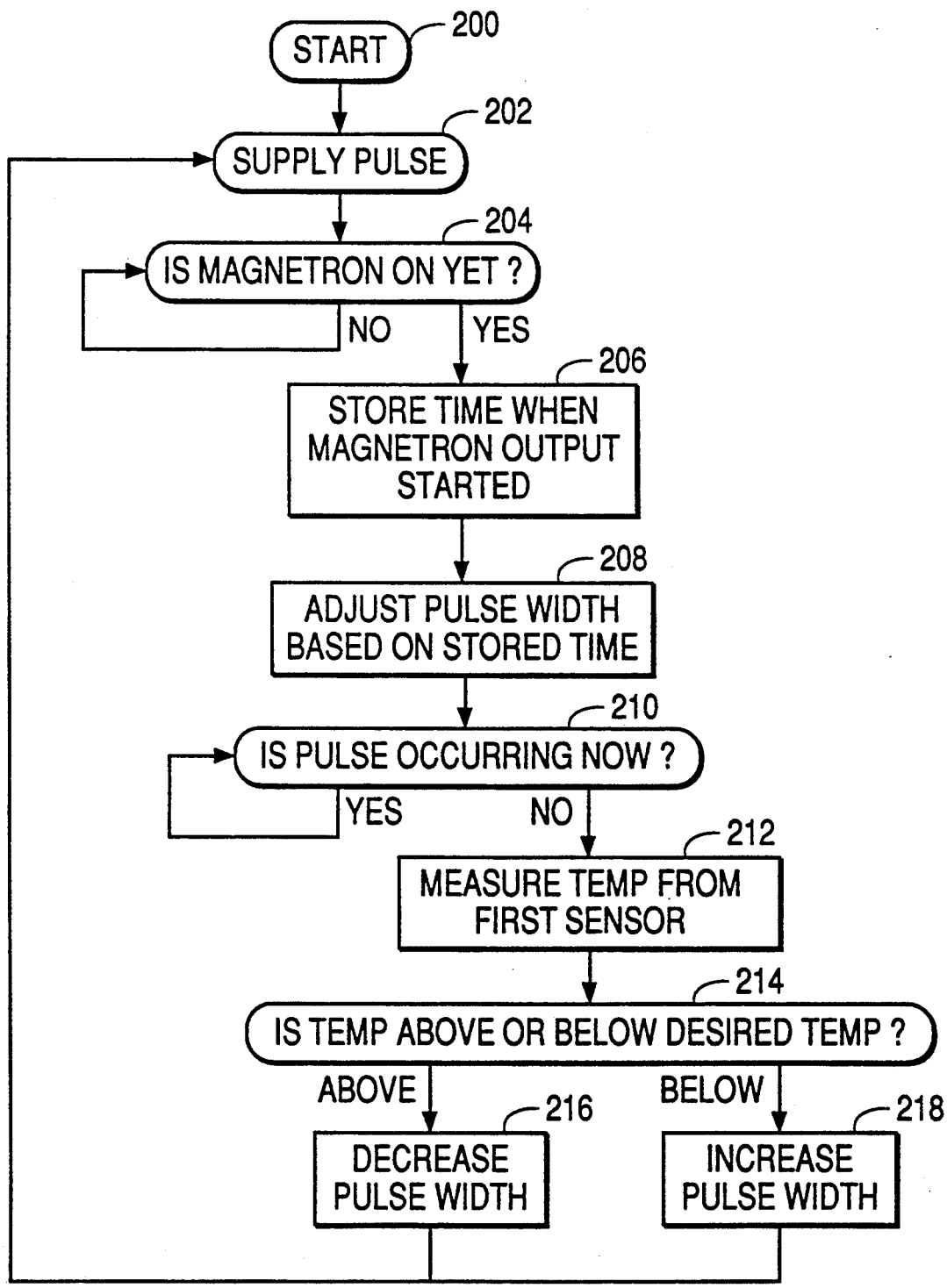
FIG. 4 shows a simplified flow chart of various steps taken by the microprocessor of FIG. 3.

In order to detect the start of microwave power generation, a small resistor 152 is placed in the A/C power line supplied to the magnetron 116M. Of course, there would be various power transformers and other components of the microwave between the A/C power line and the magnetron 116M, but such other known devices need not be shown or discussed in detail. The small resistor 152 has a primary of an isolation transformer 154 connected to it, the secondary of transformer 154 leading to a rectifier circuit 156. The output of the rectifier circuit 156 is filtered by capacitor 158 and resistor 160 and supplied to an analog to digital converter 162, the output of which is then supplied to the microprocessor 140. In the preferred embodiment, the microprocessor 140 will test 20 times per second to determine if the current sensed on the A/C power line indicates that the microwave power is being generated. The microprocessor 140 will have established a pulse width which should be supplied to the magnetron 116M to provide the desired heating of the medical fluid. However, the microprocessor 140 will note the lag time from the start of the pulse until the microwave power actually begins. The microprocessor 140 will then ignore the lag time and provide that the pulse width of the actual microwave power delivery is controlled to have the specified width. In that fashion, the variability of the start up of microwave power generation will not affect the accuracy of the control of the magnetron. Various operations of the magnetron under control of the microprocessor 140 may be accomplished using known techniques commonly used for controlling microwave ovens. However, FIG. 4 is the simplified flow chart of various aspects of operation of the present invention which are not believed to commonly be used in microwave ovens. Before discussing the details of FIG. 4, it should also be noted that attached hereto is an appendix listing the computer programs used in one implementation of the microprocessor arrangement of the present invention.

As shown in FIG. 4, the start block 200 leads to a supply pulse block 202. For the initial pulse, an initial preset value for the pulse width may be used. Following the supply of the pulse 202, block 204 tests to determine if the magnetron is on (i.e., generating microwave power). As discussed above, this may be accomplished by sensing the A/C currents supplied to the magnetron or more generally supplied to the microwave apparatus itself. If the magnetron is not yet producing microwave power, block 204 simply repeats the test. Upon microwave power generation starting, control transfers to block 206 which stores the time when the magnetron output has started. Block 206 leads to block 208 which adjusts the pulse width based on the stored time. An example may best explain this. If the pulse width is supposed to be one second long to provide the desired heating, and the delay from start of the pulse to generation of microwave power was one half second, the microprocessor will extend the pulse width an additional one half second beyond the originally planned one second. Accordingly, the total pulse width will then be one and one half seconds, but will only have one second of effective microwave power which is precisely the original planned pulse width. Thus, the time of application of microwave power is controlled accurately.

Following block 208, block 210 tests to determine if a pulse is occurring at the present time. If it is, the block simply retests this repeatedly. If the pulse has stopped, block 210 leads to block 212 which measures the temperature from the first sensor. Block 214 then tests to determine if the temperature is above or below the desired temperature. If above, the pulse width is decreased at block 216. If below, the pulse width is increased at block 218. The arrangement of blocks 214, 216, and 218 are quite simplified and, in actual practice, one may want to decrease the pulse width or increase the pulse width in an amount dependent upon the difference between the sensed temperature and the desired temperature.

Following blocks 216 and 218, control is returned to block 202 which supplies a pulse dependent upon the previous calculations.

Not shown in the simplified flow chart of FIG. 4 is a procedure for turning off the magnetron when the second sensor 122S has sensed an over temperature condition. However, this process could be implemented by simply using computer steps corresponding essentially to the arrangement of FIG. 1.

The microwave may be controlled by the microprocessor using one of several different techniques. An on-off technique involves simply turning on and off the microwave in order to provide the desired amount of power. This would be similar in concept to the thermostatic control in a house heating system, although the cycle times would of course be much faster. A second technique for controlling the microwave power is the use of a proportional integral derivative (PID) control, this being a known technique. However, the PID control did not perform very well when used in connection with the present invention. Accordingly, the preferred system for the present invention is an adaptive control based upon pulse width modulation.

Figure 5:
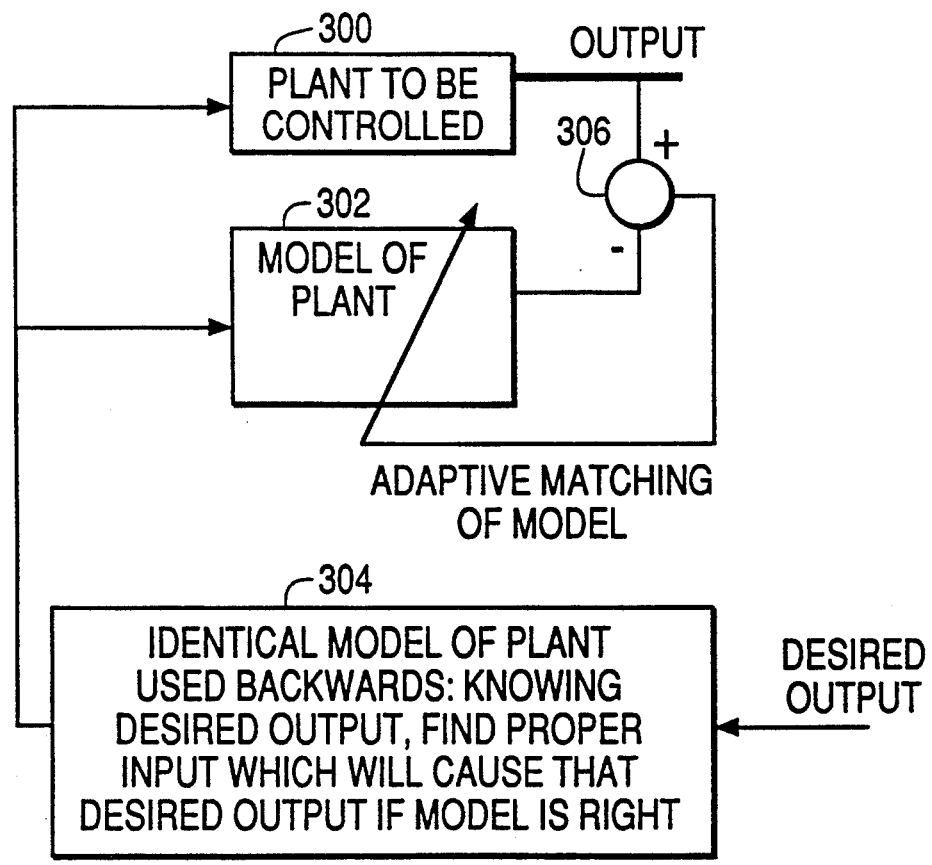
FIG. 5 is a diagram illustrating an adaptive control principle of the present invention.

The adaptive control is an arrangement which is graphically depicted in FIG. 5, this diagram being taken from chapter 11 of a book entitled Adaptive *Signal Processing*, by Bernard Widrow and Samuel D. Stearns.

The adaptive fixed impulse response filter - control method of controlling the microwave under the computer programs attached as an appendix hereto have the extremely important characteristic of being able to "learn" how to control the microwave despite changes in the performance characteristics of the chamber, magnetron, or flow state. This type of adaptive control system is believed to be required to provide the adequate temperature control and otherwise work properly. As used herein, "adaptive control" means a control arrangement which automatically "learns" from mistakes and revises its controls to become more accurate with experience.

As shown in FIG. 5, there is a plant to be controlled at block 300. In the present invention, the plant includes the microwave cavity, magnetron, and flow state or characteristics. Block 300 then represents the actual physical system. Block 302 represents a model of the plant or physical system. The desired output is supplied to block 304 as, for example, an operator indicating that the desired output should be medical fluid at 37° C. From the model of the plant, block 304 determines the inputs to the plant which will provide the desired output. For the present invention, this may be the pulse width which should provide the output of medical fluid at the desired temperature. Block 304 then provides that input to block 300 by supplying the pulse width as determined by block 304. Additionally, the pulse width is "supplied" to the model of the plant 302 within the microprocessor. The plant 300 supplies an actual output which is compared in comparator block 306 to the theoretical output supplied by the model 302. The block 306 supplies an error signal which is then used to modify the model of the plant 302 to make it more accurate.

The simplified explanation shown with respect to FIG. 5 is for a multi-compartment mathematical model built by the computer program of the "finite impulse response type." It is noted for its relative stability. For each three second time period, the magnetron is turned on for a fraction design to bring the actual temperature to the desired temperature. The mathematical model is told exactly what length of time the microwave was turned on for during the period (recall above the significance of knowing the lag time from beginning of pulse to start of microwave power) and it predicts what the output temperature will come to be. The difference between the mathematical model's prediction and the actual measured temperature is the error of the model. By use of a least means squares adaptive approach, the mathematical coefficients of the compartments of the model are adjusted so as to make the model a bit more accurate in predicting the temperature.

The model is then used to guess how to best control the actual microwave in the next three second period by mathematically solving for what input would give the desired output temperature if the model were correct. The input is then given to both microwave and model and the error - measurement and adaptive process continues.

As time goes on, the model becomes more and more accurate in predicting the performance of the actual microwave. At the same time, it gives better answers as to how to best control that microwave. Thus the system converges both to a good multi - compartment model of the microwave and to a stable temperature.

A great advantage of the adaptive approach is that if the magnetron performance changes or the fluid input temperature changes or the fluid flow changes, the model can adapt and regain control. If the mathematical model has an error of more than a set limit, a simpler type of model may be used temporarily until the model becomes more accurate. The simpler type of model may be a proportional pulse width control.

Recalling the variable time delay from power on to the start of microwave power generation, it will be appreciated that developing a stable and predictable control arrangement for a microwave oven when large volumes of fluid are passing through the oven is quite difficult. In other words, a control system which may be quite sufficient for cooking food may be completely unacceptable for providing precise temperature control within relatively short periods of time when fluid is passing through a microwave chamber. However, the present invention is able to provide such precise control.

Figure 6:
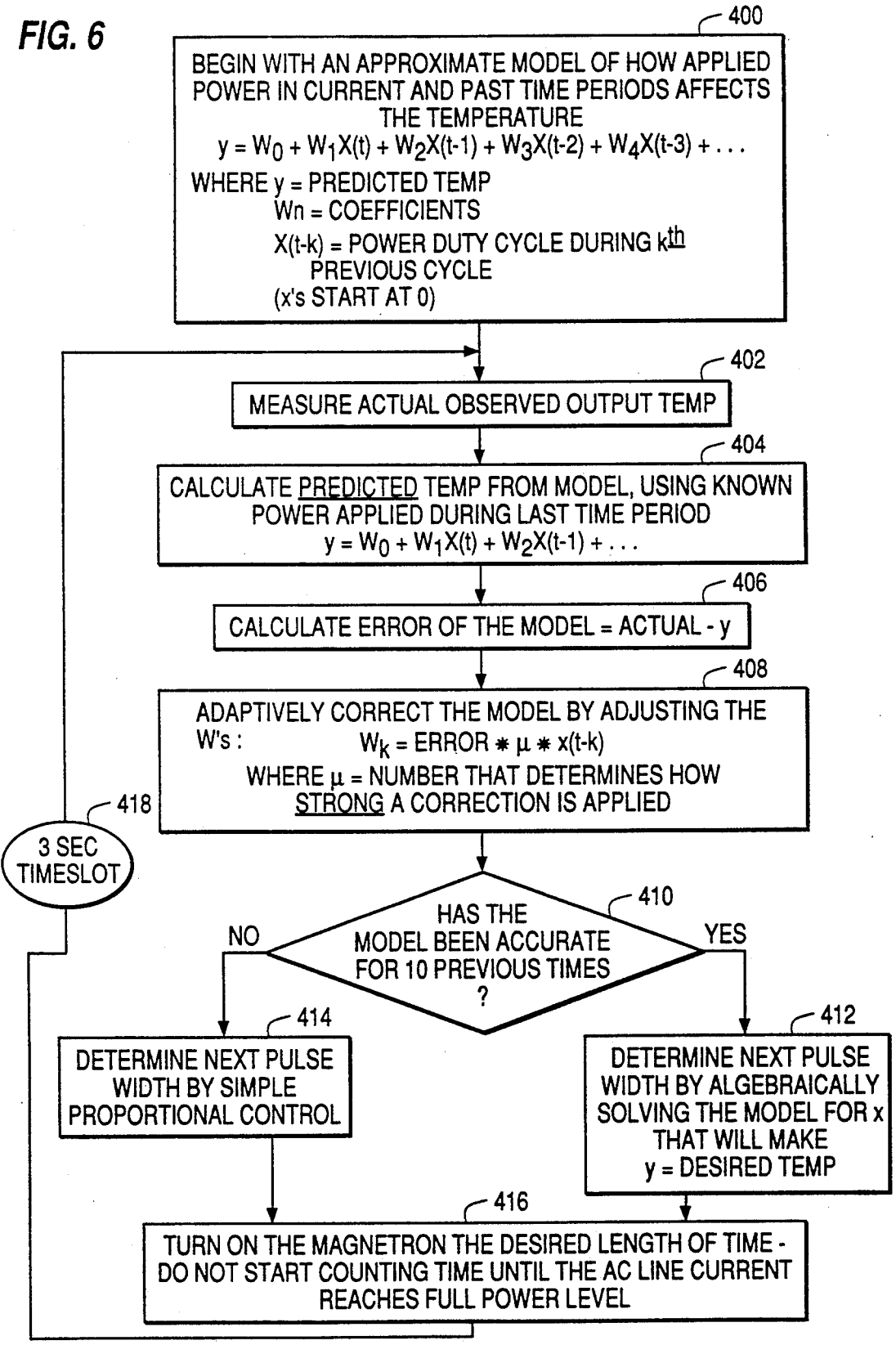
FIG. 6 is a simplified flow chart of the adaptive control features of the invention.

FIG. 6 shows a more detailed flow chart of adaptive control wherein block 400 shows how the predicted temperature is modeled. Block 402 measures actual temperature, whereas block 404 calculates predicted temperature. Block 406 calculates the error in the prediction, whereas block 408 then changes the model. If the model has been accurate for the last 10 times, block 410 leads to block 412 which calculates the pulse width based on the model. If the model has not been accurate, block 410 leads to block 414 which calculates pulse width by simple proportional control. Blocks 412 and 414 lead to block 416 which turns on the magnetron for the desired time (the lag time in microwave generation is not counted per the description with respect to FIG. 4 above). Block 416 leads to block 418 which simply represents a second time slot in which the pulse occurs, then control returns to block 402.

The adaptive control microprocessor of FIG. 3 is much superior to circuit arrangement of FIG. 1, which arrangement may not provide sufficient precision depending upon the circumstances.

One possible source of errors in the arrangement was warm air blown out of the waveguides 18F, 18S, and 18T. Specifically, the warm air blown out of the waveguides was distorting the measurements by warming the sensors 22F and 22S. This problem may be avoided by making the waveguides air tight as, for example, by putting a small, resilient ring (not shown) within each of the waveguides and closing off any space between the tube 14 (for waveguides 18F and 18S) and the waveguides. A similar resilient ring (not shown) could be used within the third waveguide 18T to seal that waveguide air tight.

Although specific constructions and arrangements have been presented herein, it is to be understood that these are for illustrative purposes only. Various modifications and adaptations will be apparent with those of skill in the art. For example, the tube 14 is shown with the inlet 16N and outlet 16U on opposite sides of the microwave 16. However, the tube 14 is sufficiently flexible that one could alternately simply have the tube 14 extend in a loop or half loop within the microwave cavity. Further, the present invention as described herein has used a microwave apparatus, however alternate devices which provide for electromagnetic radiation heating of medical fluids could be used. Further, the sensors 22F and 22S receive waves of energy which are thermal waves of energy transmitted by radiation, but other waves which are non-conductively transmitted over at least part of their path could be supplied to the sensors 22F and 22S. The sensing is non-invasive meaning that nothing extends inwardly beyond the normal inside diameter of the tube 14. The window or thin membrane portion 20F serves as an accommodation means to accommodate waves of energy supplied to the sensors. The windows such as 20F and 20S supply the infrared energy by transmission therethrough.

The windows or thin membrane portions 20F and 20S are shown fixed to the tube 14. However, one could alternately provide the windows are part of a coupler member which attaches between two different sections of the tube. The coupler could still be considered part of the tube or mounted to the tube, but the mounting would not be as direct as with the illustrated embodiment. Sensors 22F and 22S in FIG. 1 (or the similar first and second sensors in FIG. 3) could have their locations changed. For example, the second sensor 22S could be located at the input side of the microwave 16 so as to sense the temperature of the incoming medical fluid before it is heated and could be used to supply an input to the feedback control of the magnetron so that the microwave heat is adjusted depending on the temperature of the fluid before it is heated. A single sensor system might have a sensor mounted like sensor 22S of FIG. 1 except positioned to sense fluid temperature just inside of the exit port 16U. Such a single system might be used for both feedback control and overtemperature protection, thereby performing the functions of both sensors in the arrangements of FIGS. 1-3. To allow such a sensor (which detects temperature of fluid within the microwave) to minimize errors which might otherwise result from convection air currents or other problems, one might use a plastic ring around the thin membrane or window portion of the tube to shield the window from such currents. Further, the first sensor 22F could be located immediately adjacent to the catheter whereat the medical fluid goes into the patient. By locating the first sensor immediately next to the patient, one can have the system adjust for the cooling down of the fluid as it passes from the microwave apparatus to the patient. A more complex control strategy may involve using more than two sensors and using two or more sensors for input signals to the feedback control loop operating the magnetron. In view of the numerous modifications and adaptations which are possible, it will be readily appreciated that the scope of the present invention should be determined by reference to the claims appended hereto.

APPENDIX

```
/*---------------------------------------------------------*/
/*                    AMC.C                              */
/*      COPYRIGHT 1990-University of Florida              */ include <stdio.h>
include <io515.h>
#include "read_ad.c"
#include <int_addr.h>
#include "clk727.c"

#define SCALE     0.178
#define OFFSET    0.5
#define SET_TEMP  38.0
#define INCREMENT 1
define ORDER     20 define PERIODSPERMINUTE      20
define SECONDSPERPERIOD       3
#define OBSMINS                5  /* number of minutes of observation max*/
```

```c
#define ERRORLIMIT    3  /* maximum degrees allowable of
model                       error */

/* NOTE THERE ARE TWO SCALES in this program.
        SCALE is related to the temperature conversions,
        scale is a factor applied to mu (originally 0.0001)
---------------------------------------------------------*/ extern int pw;        /* the pulse width 0-100 to be used in next period*/ extern int per;
extern unsigned char temp;
extern unsigned char current;   /* proportional to current in AC line */
    /* read inside interrupt routine  inc_sysclk */ extern int read;
extern unsigned char deadtime;
extern unsigned char lastdeadtime;

void main()
{
   float w[ORDER+1], xk[ORDER+1], err, yk, t1, mu=0.000001;

int scale, ptr=1 ;   /* 1based array, not 0 based */
   register int i,j;
   int    order;
   int    timecounter;  /* periods passed, rezeroed every minute */
   int    minutes;      /* minutes passed */
   float  observedtemperature;  /* actual measured temperature */
   int    zeroes;
   int    inputtemp;
   int    mult;         /* multiplier for initials w[x] */
   float  switchovertime ;  /* minutes before model became sufficiently
                               accurate */ float   minutemax; /* current max for this minute */
        float   minutemin; /* current min for this minute */
        int     switchovercounter;  /* reset to 0 whenever the
                                       system has to abandon model */
        int     finetune; /* allow simple controller to step up a bit */
        int     startupcounter=0; /* counts first 30 iterations from
                                     any temp < 30 and restarts slowly */

/*--------Explanation of variables:--------------------------------- w[]  = Weights xk[] = Output to Microwave ( pulse width )

yk   = Output of Adaptive Model ( should match actual Micro output

---------------------------------------------------------------*/
```

```c
/* -------------------- Set up Model Control -------------------- */

MICRO_OFF;   /* switch off microwave when program begins */ printf("*****************WARMER ADAPTIVE CONTROL************\n");

printf("Original Mu = %f \n",mu);

printf("Multiply MU by ? xxx :");

scale=(getchar()-48) * 100;

scale = scale + (getchar()-48)*10;

scale = scale + (getchar()-48);

getchar();

printf("Scale = %d\n",scale);
mu=mu*    ((float)scale);
printf("MU = %f\n",mu);
printf("Enter 2-digit order: xx \n");
     order = (getchar()-48)*10;
     order = order + (getchar()-48);
     getchar();
printf("Order of Fit = %d \n",order);
printf("Enter # coeff to be zeroed:\n");
zeroes = getchar()-48;
        getchar();
printf("Zeroes = %d \n",zeroes);
printf("Enter input temp: xx \n");
inputtemp = (getchar()-48)*10;
inputtemp = inputtemp + (getchar()-48);
           getchar();
printf("Input temp = %d \n",inputtemp);
/*------------------------- Initialize Coefficients----------------*/
w[0] = (float)inputtemp;  /* somewhere between 0 & 25 */
             /* should be the INPUT TEMPERATURE!! */
printf("Initial w[x] = 0.01. Multiple: x \n");
mult = getchar()-48;
getchar();
printf("Degrees above 35 to allow simple controller? ");
finetune = getchar()-48;
printf("Switch ON the microwave and hit ENTER to begin\n");
 getchar();
for(i=1; i<=order; i++)
   {
     w[i] =  0.01*mult;                /* 0.25/(ORDER-2)  */
     xk[i] = 0;
   } for(i=1;i<=zeroes;i++) w[i]=0;
  pw = 0;
       switchovertime   =   -1;  /* neg 1 to show not switched */
       minutemax        =       -100;
       minutemin        =       500;
    switchovercounter =          0;
       minutes = 0;
        timecounter = 0;
```

```
/* -------------------- Begin adaptation-------------------------*/
  enable_sysclk();
  while(TRUE)
    {
      while( read == FALSE );   /* wait for OFF state */
/* if(pw>90) pw=10;
      else pw=5;
*/
     read = FALSE; /* reset the flag */
     yk = w[0];
     /* On first pass, w[1]->xk[2] w[15]->xk[1] */
     for(j=1, i=ptr+1 ; j <= order ; j++,i++)
        {
          if( i > order ) i=1;
          /* this implements a ring cross correlation in place */
          yk =   yk + w[j]*xk[i];
        } observedtemperature = (float)(temp) * SCALE;
     if(observedtemperature < 25)
        {
          startupcounter = 22;
             printf("Slow Startup Activated\n");
        } if(startupcounter > 0)
        {
         startupcounter--;   /* may become negative ? */
         if (startupcounter < 0) startupcounter = 0;
         printf("Startupcounter:   %d \n",startupcounter);
        } err = observedtemperature - yk;

/* ---------- Updates: ADAPTIVE FITTING OF THE MODEL -----------*/
     w[0] = w[0] + mu*err*20;
     for(j=1, i=ptr+1 ;j<=order; j++,i++)
      {
        if(i>order)i=1;
        w[j] = w[j] + mu*err*xk[i];
      } for(i=1;i<=zeroes;i++) w[i]=0;
             /* corresponding to the transport delay, see elsewhere!*/

/* ------------------ Forward Calculation --------------------- */ for( t1=0, j=1, i=ptr; j<=order; j++,i++)
     /* NOTES:  3/24 changed this fromi=ptr+1 to i=ptr to accomplish
                 the time slide.  Also made j<ORDER instead of j<=ORDER
                 because in the prediction of next move, should have
                 one less term, as we are FINDING that last term! */
     {
       if(i > order)i=1;
       if( j != zeroes+1 ) t1 = t1 + w[j]*xk[i];
     }

/* ptr++; */
     /* if( ptr > ORDER ) ptr=1; */
```

```
        /* note that yk = w0 + summation of all those in t1 */ if( w[zeroes+1] != 0) xk[ptr] = ( SET_TEMP - w[0] - t1
)/w[zeroes+1];

/* becasuse w1 and w2 ,,,are zero!! Transport delay */
        /* xk is the predicted correct amount of time to leave
           the microwave on, as a 0-100 scale of the next
           time period*/
    else xk[ptr] = 100;
    if(xk[ptr]>95) xk[ptr] = 95;
    if(xk[ptr]<0 ) xk[ptr] = 5;
    /*------------------------SIMPLE CONTROLLER----------------*/
    if( ( err >= ERRORLIMIT) || (err <= -ERRORLIMIT) ||
(switchovercounter<=10000) )
    {
    printf("USING SIMPLE CONTROLLER\n");
    if( err>=ERRORLIMIT || err <= -ERRORLIMIT ) switchovercounter = 0;
    else switchovercounter++;

/* model OK but not yet OK for enough periods*/
            /* reset the counter of # good model periods*/ if(observedtemperature > SET_TEMP -3 +finetune)
            {
                /* temp too hot */
                xk[ptr] = 0; /* with new measurement, don't need
prewarm*/
                pw = xk[ptr];

} else
            { /* Proportional Control (believe it or not) */
                xk[ptr] = 5*(    SET_TEMP
                            - (startupcounter/3)
                            - observedtemperature
                            + finetune);
            /* Adjustment for the 50% turn on delay: */
            /* linear scale 0-30 */

/*  if(xk[ptr] > 30) xk[ptr] = 30;
            pw = xk[ptr] + 40;
            if (pw>70) pw= 70;
    no longer needed because of our repairs! */
    if(xk[ptr]<0) xk[ptr]=0;
    if(xk[ptr]>90) xk[ptr]=90;
    pw=xk[ptr];
        } printf("Current DeadTime Measurement:  %u \n",lastdeadtime);

/* NOTE MUST KEEP MODEL INFORMED OF WHAT WE ARE DOING! */

} /* end of the case that we are not ready for model control */

/*-----------------------END-------------           --------*/

/*----------------------MODEL CONTROLLER-------------------*/

/* if the model has been sufficiently accurate, use the model*/ else    /* we were within the error limits */
```

```
        {
            switchovercounter-- ; /* increment the good counter */
            /*..........calculate out the correct time period........*/ pw = xk[ptr];
        }
            /* now that we have finished calculating the control,
                by whatever method, we can spend the time to do
               other calculations */

/* now move forward in the ring buffer of xk's */ ptr-- ;
if(ptr<1) ptr=order ;   /* 0 becomes 15 */ timecounter++;
            if(timecounter >= PERIODSPERMINUTE)
                {
                /* this first happens at the end of the 0th minute */
                    minutes++;
                    timecounter = 0;
                minutemax            =          -100;
                    minutemin        -          500;
                    printf("Minute #%d \n",minutes);

for(i=0;i<=order-1;i++) printf("w[%d] = %f \n",i,w[i]);

} if(observedtemperature>minutemax) minutemax = observedtemperature;
        if(observedtemperature<minutemin) minutemin = observedtemperature;
printf("T=%4f\tW[0]=%f\tW[%d]=%f\tERR = %3.5f\tyk = %f\nPW = %d\n",
            observedtemperature, w[0],zeroes+1, w[zeroes+1], err, yk,pw);
            printf("Switch count = %d \n\n",switchovercounter);

} /* end of endless loop */

} /* end of the MAIN subroutine */
/* These system clock routines written by Ron Carovano 6/89

SYSCLK is a global unsigned integer variable that is incremented every
    0.05 seconds.  Timer 2 on the 80535 was used to accomplish proper
    timing.

ENABLE_SYSCLK enables the timing system.  The bits of the timer 2 control
    register (T2CON) are configured as follows:

T2PS = 0; this clocks timer 2 every microsecond
            T2R1 = 1, T2R0 = 0; this reloads the timer registers TH2|TL2 with
                               the reload value in CRCH|CRCL.  The reload
                               value is such that timer overflow interrupts
                               every tenth of a second
            T2I1 = 0, T2I0 = 1; select timer function Other bits that are wiggled:

These bits are in the register IEN0
            EAL = 1; enables all interrupts
            ET2 = 1; enables timer 2 overflow interrupt This bit is in IRCON
            TF2 = 0; this bit flags a timer 2 overflow INC_SYSCLK is the interrupt routine that increments the variable SYSCLK
    every tenth of a second.  TF2_bit is cleared to re-enable the interrupt.
```

```c
*/
unsigned long int sysclk=0;
unsigned char temp=0;
unsigned char current =0;   /* to hold AC line current for main()  */
unsigned char deadtime=0;   /* number of 20ths of a second before current
seen*/
unsigned char lastdeadtime=0; /* stored value of last dead time for use
                                by other programs */ extern void tf2_isr();

define PERIOD  60.0  /* 3.0 seconds */
#define MICRO_ON   set_bit (P3_2_bit)
#define MICRO_OFF  clear_bit (P3_2_bit)
#define READ_TEMP  read_ad(0,&t)
#define TRUE     1
#define FALSE    0
define DONE     2 int read = FALSE;
int per = 0;  /* counter for period */
int pw = 0;    /* Pulse Width may take values from 5 - 95 %  */ void enable_sysclk()
{
   int addr = (int) tf2_isr;
   write_XDATA (0x802d,addr);
   write_XDATA (0x802c,addr>>8);
     output(CRCH,0x3c);
     output(CRCL,0xb0);
     output(TH2,0x3c);
     output(TL2,0xb0);
     clear_bit(T2PS_bit);
     set_bit(T2R1_bit);
     clear_bit(T2R0_bit);
     clear_bit(T2I1_bit);
     set_bit(T2I0_bit);
     set_bit(EAL_bit);
     set_bit(ET2_bit);
     clear_bit(TF2_bit);
}
void inc_sysclk()
{
 /* not sure whether this routine is entered 10 or 20 times per second!!*/ int i,val=0;
   unsigned char t;
   per++;  /* equal to the number of twentieths of seconds past
             in this warming period of 3 seconds (see PERIOD above )*/ read_ad(1,&current);
   if( current < 50) deadtime++;

/* NOW, determine whether to turn on the microwave: */
   if(     ((per-deadtime)< (int)( (float)pw*PERIOD/100.0))
           && (per < PERIOD)         )
      {
      MICRO_ON;
      }
```

```
    else
    {
      MICRO_OFF;
    } if( per >= (int)(PERIOD+2.5) )
    {
        val = 0;
      per=0;
      for(i=0;i<=20;i++)
        {
          READ_TEMP;
          val = val + t;
        }
      lastdeadtime = deadtime;
      deadtime = 0;

temp = val/20;
        read = TRUE;    /* flag to notify polling routine data is avail */

} sysclk += 1;
        clear_bit(TF2_bit);
  }
```

What is claimed is:

1. A system for in-line heating of medical fluids supplied to a patient comprising:
   a heating apparatus for radiant heating by electromagnetic radiation including a source of electromagnetic radiation, a housing and a zone for heating within said housing, said housing having an inlet for entry of medical fluids into said zone while said source is generating electromagnetic radiation and an outlet for exit for medical fluids while said source is generating electromagnetic radiation for heating medical fluids flowing in a path between said inlet and outlet;
   a first sensor for sensing the temperature at a first location of medical fluid heated by said heating apparatus and generating a first output representative of sensed temperature, said first sensor sensing temperature by receiving optical waves of energy;
   a controller for receiving said first output and providing feedback control of said source to minimize differences between the sensed temperature of the medical fluid and a desired temperature for the medical fluid; and
   a tube for carrying medical fluid therein at least in said zone between said inlet and said outlet and defining said path, said first sensor sensing temperature by nonconductively sensing infrared energy from the medical fluid, at least some of which has passed through at least part of said tube, from at least one of said tube and the medical fluid at said first location for sensing temperature of medical fluid within said tube, said first location being within said tube, said first sensor being separate from said tube, and said tube including a thin membrane portion to allow infrared energy to pass therethrough to said first sensor.

2. An invention for in-line heating of medical fluid supplied to a patient comprising a tube for carrying medical fluid, said tube having a thin membrane portion thinner than a remainder portion of said tube and allowing passage of infrared energy from medical fluid therein to outside of said tube, said tube being disposable and adapted for being removably positioned in a microwave apparatus.

3. The invention of claim 2 further comprising a microwave apparatus and a first sensor for sensing temperature of medical fluid by receiving infrared energy which has passed through said thin membrane portion, said tube being disposed in said microwave apparatus.

* * * * *

UNITED STATES PATENT AND TRADEMARK OFFICE
CERTIFICATE OF CORRECTION

PATENT NO.   :   5,180,896
DATED        :   January 19, 1993
INVENTOR(S)  :   Gordon L. GIBBY, ET AL It is certified that error appears in the above-identified patent and that said Letters Patent is hereby corrected as shown below:

On title page, item [73] Assignee: "Gainseville" should read --Gainesville--.

Column 30, line 39, after "portion" insert
-- thinner than a remainder portion of said tube --.

Signed and Sealed this

Twenty-sixth Day of October, 1993

Attest:

BRUCE LEHMAN

Attesting Officer          Commissioner of Patents and Trademarks